United States Patent

Tokuyasu et al.

[11] Patent Number: 6,127,464
[45] Date of Patent: Oct. 3, 2000

[54] PHOSPHORIC ESTER, PROCESS FOR PREPARING THE SAME AND USE THEREOF

[75] Inventors: Noriaki Tokuyasu, Ikoma; Tadanori Matsumura, Higashiosaka, both of Japan

[73] Assignee: Daihachi Chemical Industry Co., Ltd., Osaka, Japan

[21] Appl. No.: 09/198,456

[22] Filed: Nov. 24, 1998

[30] Foreign Application Priority Data

Dec. 19, 1997 [JP] Japan ................................. 9-351486

[51] Int. Cl.⁷ .................. C08K 3/32; C07F 9/09
[52] U.S. Cl. .................. 524/117; 558/105; 558/117; 558/86; 524/118
[58] Field of Search .............. 558/86, 117, 105; 524/117, 118

[56] References Cited

U.S. PATENT DOCUMENTS

| 2,372,244 | 3/1945 | Adams et al. | 558/105 |
|---|---|---|---|
| 3,006,946 | 10/1961 | Lanham | 558/86 |
| 3,652,743 | 3/1972 | Harris et al. | |
| 5,017,650 | 5/1991 | Nakamura et al. | 525/65 |
| 5,401,788 | 3/1995 | Tokuyasu et al. | |
| 5,750,601 | 5/1998 | Staendeke | |

FOREIGN PATENT DOCUMENTS

| 0005329 | 11/1979 | European Pat. Off. |
|---|---|---|
| 617042 | 3/1994 | European Pat. Off. |
| 779332 | 6/1997 | European Pat. Off. |
| 55-110175 | 8/1980 | Japan . |
| 57-125259 | 8/1982 | Japan . |
| 58-117272 | 7/1983 | Japan . |
| 6-321974 | 11/1994 | Japan . |
| 1436553 | 5/1976 | United Kingdom . |
| 2043655 | 10/1980 | United Kingdom . |

OTHER PUBLICATIONS

English Language Abstract of JP No. 6–321974.
English Language Abstract of JP No. 57–125259.
Patent Abstract of Japan, vol. 006, No. 223 (C–133), of JP–A–57–125259.
*Organo–Phosphorus Compounds* by Kosolapoff, John Wiley & Sons, p. 230, 1950.

Primary Examiner—Robert Dawson
Assistant Examiner—Kuo-Liang Peng
Attorney, Agent, or Firm—Greenblum & Bernstein, P.L.C.

[57] ABSTRACT

A flame retarder containing a phosphate obtained by reacting a compound represented by the general formula (II):

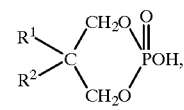

(II)

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, with at least one compound represented by the general formula (III):

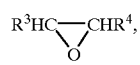

(III)

wherein $R^3$ and $R^4$ are, the same or different, a hydrogen atom or a straight or branched-chain alkyl group having 1 to 8 carbon atoms.

14 Claims, 8 Drawing Sheets

PHOSPHORIC ESTER, PROCESS FOR PREPARING THE SAME AND USE THEREOF

CROSS-REFERENCE TO RELATED APPLICATION

This application is related to Japanese application No. HEI 9(1997)-351486, filed on Dec. 19, 1997, whose priority is claimed under 35 USC § 119, the disclosure of which is incorporated by reference in its entirety.

BACKGROUND OF THE INVENTION

1. Field of the Invention

The present invention relates to a phosphoric ester (hereinafter referred to as phosphate for simplicity), a process for preparing the same and use thereof. More particularly, the invention relates to a non-halide phosphate having a phosphorinane structure and a hydroxyl group, a process for preparing the same and a flame-retarder and a flame-retarded resin composition containing the same.

2. Description of Related Art

Thermoplastic resins such as polypropylene, polystyrene or acrylonitrile-butadiene-styrene (ABS) resin and thermosetting resins such as polyurethane or phenolic resin have excellent characteristics of being able to be produced at relatively low costs, to be easily formed or the like. Accordingly, these resins are widely used for general daily goods including electronic parts and automobile parts. However, these thermoplastic resins and thermosetting resins (hereinafter referred to as resins) fire readily, and therefore, they easily burn or burn out once they catch fire. Especially a fire at public facilities such as electric facilities and communication cables may cause great damage to functions of a community.

For this reason, flame retardancy is required by laws in some fields such as electric appliances, automobile interiors, and textile fabrics for which such resins are used. Such flame retardancy regulations are known as the UL standard for electric appliances and as MVSS-302 for automobile-related products in the United States, for example.

For providing flame retardancy to a resin, a flame-retarder is generally added in preparation for resin products. Used as flame-retarders are inorganic compounds, organic phosphorus compounds, organic halogen compounds, organic phosphorus compounds containing halogens and the like.

Among the above-mentioned compounds, halogen compounds such as organic halogen compounds and organic phosphorus compounds containing halogens exhibit an excellent flame-retardant effect. These compounds, may however, generate a hydrogen halide by pyrolysis when resin products are molded. Hydrogen halides cause problems such as corrosion of metal molds, deterioration and coloration of resin itself. Furthermore, since hydrogen halides are toxic, they not only change work environment for the worse but also generate toxic gases such as hydrogen halide and dioxins, when burning, for example, in a fire, so that it produces ill effects on humans.

Inorganic compounds such as magnesium hydroxide and aluminum hydroxide are known as flame-retarders that do not contain halogens. However, these flame-retarders have only significantly poor flame-retardant effect. They need to be added to resins in great amount in order to exhibit sufficient effect, and as a result, deteriorate the properties of the resin itself.

For the above reasons, organic phosphorus compounds are generally used as flame-retarders exhibiting relatively good flame-retardant effect but not containing halogens. Typical examples of organic phosphorus compounds include aromatic phosphorus compounds such as triphenyl phosphate (TPP), tricresyl phosphate (TCP) and cresyldiphenyl phosphate (CDP). These are used as flame-retarders for a variety of engineering plastics such as phenol resin, epoxy resin and polyurethane.

These organic phosphorus compounds, especially TPP, have a low content of phosphorus, to which their flame retardancy is attributed, and therefore, are usually used as a mixture with halogen compounds to provide satisfactory flame-retardancy for resins. In the case where TPP is used alone, TPP must be added to resins in large amount and therefore may deteriorate the properties of the resins itself.

Japanese Unexamined Patent Publication No. SHO 55(1980)-110175 discloses the following compound as an additive providing flame retardancy to resins:

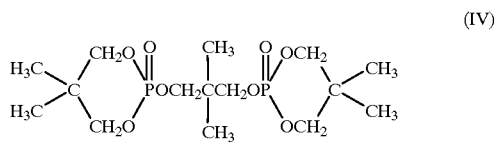

(IV)

Japanese Unexamined Patent Publication No. HEI 6(1994)-321974 discloses the following compound as an additive providing flame retardancy to resins:

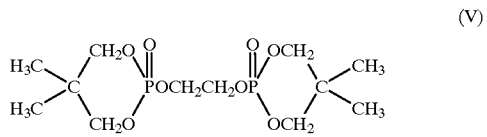

(V)

The above-mentioned compounds (IV) and (V), however, are solid. Therefore, it is difficult to add these compounds to resins, especially polyurethane foam, in a desired amount at a molding process. These compounds, when used, are pre-dispersed in polyol which is a raw material for resin in some cases. However, the dispersion of the compounds is not satisfactory because of their sedimentation. Furthermore, these compounds must be added to polyurethane foam in large amount to provide sufficient flame retardancy thereto, and therefore, significantly deteriorate the properties of this resin.

Japanese Unexamined Patent Publication No. SHO 58(1983)-117272 discloses a flameproofing agent composed of poly(oxyorganophosphate/phosphonate). This compound has a high phosphorus content (P%) and is excellent in flame retardancy, but does not have sufficient performance in either thermal resistance or resistance to hydrolysis. Further, the compound have some drawbacks, for example, in that it affects the natural properties of resins adversely and that it brings difficulty to the molding process.

Japanese Unexamined Patent Publication No. SHO 57(1982)-125259 discloses the following compound (39) as a stabilizer which provides weathering resistance and thermal stability to halogen-containing resins, though this compound is not a flame-retarder. This publication does not discuss flame-retarders for the resins.

(39)

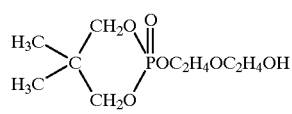

SUMMARY OF THE INVENTION

The present invention provides a flame retarder containing a phosphate obtainable by reacting a compound represented by the general formula (II):

(II)

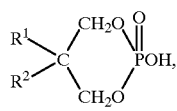

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, with at least one compound represented by the general formula (III)

(III)

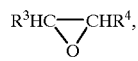

wherein $R^3$ and $R^4$ are, the same or different, a hydrogen atom or a straight or branched-chain alkyl group having 1 to 8 carbon atoms.

The present invention also provides a flame retardant containing a phosphate represented by the general formula (I):

(I)

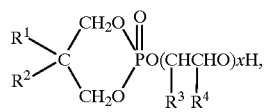

wherein $R^1$ and $R^2$ have the same meaning as defined in the general formula (II), $R^3$ and $R^4$ have the same meaning as defined in the general formula (III) and x is an integer of 1 to 9.

Further, the present invention provides a resin composition comprising a thermoplastic or thermosetting resin and the above-described phosphate in an effective amount as a retarder.

Further, the present invention provides a process or preparing a phosphate, the process comprising reacting a compound represented by the general formula (II):

(II)

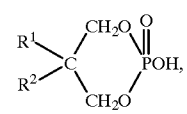

wherein $R^1$ and $R^2$ have the same meaning as defined above, with a compound represented by the general formula (III):

(III)

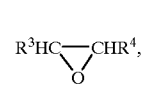

wherein $R^3$ and $R^4$ have the same meaning as defined above, to obtain a phosphate represented by the general formula (I):

(I)

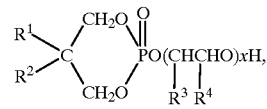

wherein $R^1$, $R^2$, $R^3$, $R^4$ and x have the same meaning as defined above.

Further, the present invention provides a phosphate represented by the general formula (I'):

(I')

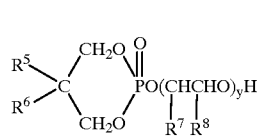

wherein $R^5$ and $R^6$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, $R^7$ and $R^8$ are, the same or different, a hydrogen atom or a straight or branched-chain alkyl group having 1 to 8 carbon atoms, and y is an integer of 1 to 9, but y is not 2 provided that both $R^5$ and $R^6$ are methyl and both $R^7$ and $R^8$ are a hydrogen atom.

Further, the present invention provides a phosphate represented by the general formula (II):

(II)

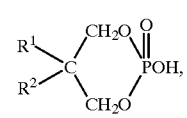

wherein $R^1$ and $R^2$ have the same meaning as defined above.

DESCRIPTION OF THE PREFERRED EMBODIMENTS

Figure 1:
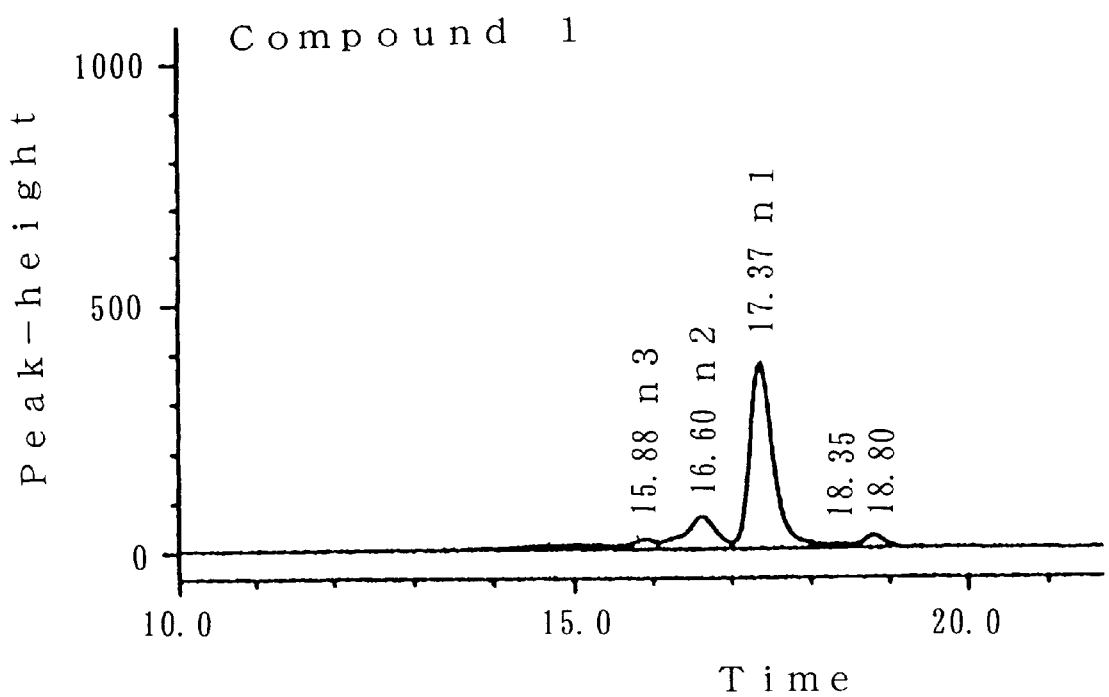
FIG. 1 shows a result of GPC of a phosphate (Compound 1) in accordance with Example 1 of the present invention.

The present invention is to solve the above-described defects of the conventional arts, and an object of the present invention is to provide novel compounds not containing any halogen which is able to be used as a flame-retarder to provide excellent flame retardancy to various kinds of resins and a process for preparing the same. The novel compounds also have an excellent thermal resistance and cause less deterioration of the intrinsic properties of the resins with which the compound is used, e.g., in the molding of the resins.

Another object of the invention is to provide a flame-retarder containing the above-mentioned novel compound and a flame-retarded resin composition containing the novel compound and a resin. The flame-retarded resin composition is excellent in thermal resistance, has an excellent long-lasting flame retardancy and can form articles which do not produce drips of molten resin when burned.

After intensive study, inventors of the present invention have found that it is possible to give an excellent thermal resistance and flame-retardancy to resins without impairing the properties of the resins by adding to the resins a phosphate obtained by the below-described reaction, especially a phosphate represented by the following formula. Since it does not contain any halogen, the phosphate does not produce a harmful or toxic gas such as hydrogen halide, does not have ill effect on humans or does not cause corrosion to a metal mold. Further articles of resins free of deterioration can be formed. From these findings, the inventors have achieved the present invention.

The phosphate contained in the flame-retarder of the present invention is obtained by reacting a compound of the general formula (II) with at least one compound of the general formula (III). This reaction will be described in detail later in this specification.

The phosphate obtained by the above-mentioned reaction is represented by the general formula (I), for example. In the general formula (I), the substituents $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, $R^3$ and $R^4$ are, the same or different, a hydrogen atom or a straight or branched-chain alkyl group having 1 to 8 carbon atoms, and x is an integer of 1 to 9.

Examples of the straight or branched-chain alkyl groups having 1 to 8 carbon atoms include straight-chain alkyl groups such as methyl, ethyl, n-propyl, n-butyl, n-pentyl, n-hexyl, n-heptyl and n-octyl; and branched alkyl groups such as iso-propyl, iso-butyl, sec-butyl, tert-butyl, iso-pentyl, tert-pentyl, neo-pentyl, iso-hexyl, methylhexyl, methylheptyl, dimethylhexyl and 2-ethylhexyl, among which lower alkyl groups having 1 to 4 carbon atoms such as methyl, ethyl, n-propyl, n-butyl, iso-propyl, iso-butyl, sec-butyl and tert-butyl are preferable and methyl and ethyl are particularly preferable.

Examples of the alkenyl groups having 2 to 8 carbon atoms include vinyl, allyl, isopropenyl, butenyl, pentenyl, hexenyl, heptenyl and octenyl, among which allyl is particularly preferable.

Examples of the optionally substituted aryl groups having 6 to 12 carbon atoms include phenyl, (o-, m-, p-)cresyl, (o-, m-, p-)tolyl, (2,3-, 2,4-, 2,5-, 2,6-, 3,4-, 3,5-)xylyl, mesityl, trimethylphenyl, ethylphenyl, propylphenyl, butylphenyl, nitrophenyl, methoxyphenyl and naphthyl, among which phenyl, cresyl and xylyl are particularly preferred.

The alicyclic hydrocarbon groups having 3 to 12 carbon atoms include saturated and unsaturated alicyclic hydrocarbon groups, of which the saturated alicyclic hydrocarbon groups are preferable. Preferable examples of the saturated alicyclic hydrocarbon groups include cyclopentyl, cyclohexyl and cycloheptyl, among which cyclohexyl is particularly preferable.

Preferable examples of aralkyl groups having 7 to 12 carbon atoms include benzyl and phenetyl, of which benzyl is particularly preferable.

In the general formula (I), the substituents $R^3$ and $R^4$ are, the same or different, a hydrogen atom or a straight or branched-chain alkyl group having 1 to 8 carbon atoms. Examples of the straight or branched-chain alkyl groups having 1 to 8 carbon atoms include the same groups as listed for the substituents $R^1$ and $R^2$. As for the substituent $R^3$ and $R^4$, hydrogen atom, methyl, ethyl, n-propyl, n-butyl, iso-propyl, iso-butyl, sec-butyl and tert-butyl are preferable, among which hydrogen atom, methyl and ethyl are particularly preferable.

In the general formula (I), x indicates the number of repetitions of the constituent unit in the parentheses, and x is, for example, an integer of 1 to 9, preferably 1 to 5, more preferably 1 to 2.

The phosphate of the general formula (I) may be a mixture of compounds having different constituent units in the parentheses. In such cases, x indicates a mean value.

Preferable examples of the phosphates of the general formula (I) include the following compounds (1) to (39), among which the compounds (1) to (16), (23) to (31) and (39) may suitably be used. These compounds may be used individually or as a mixture of two or more thereof.

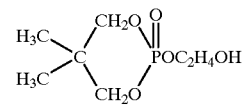

(1)

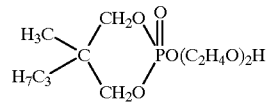

(2)

-continued
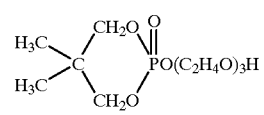 (3)
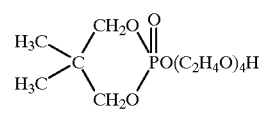 (4)
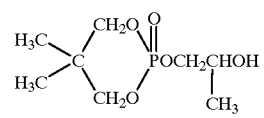 (5)
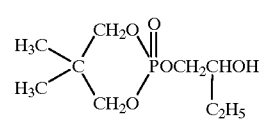 (6)
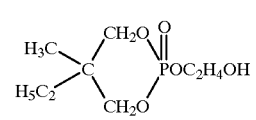 (7)
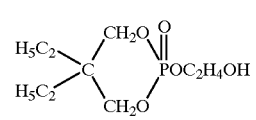 (8)
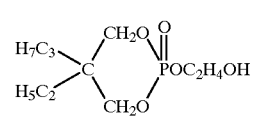 (9)
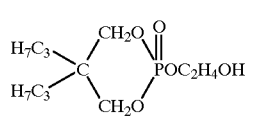 (10)
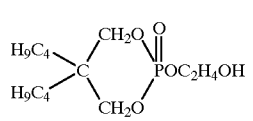 (11)
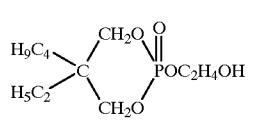 (12)
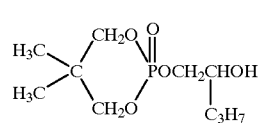 (13)
-continued
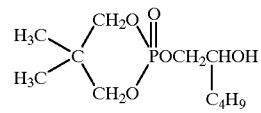 (14)
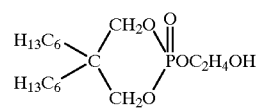 (15)
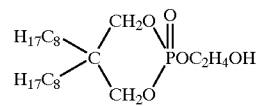 (16)
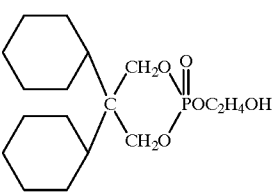 (17)
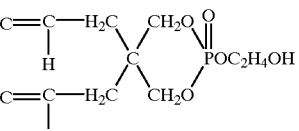 (18)
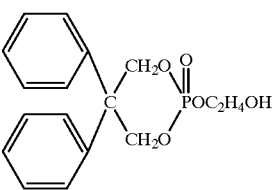 (19)
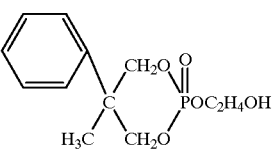 (20)
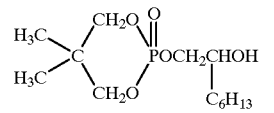 (21)
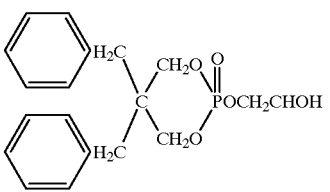 (22)

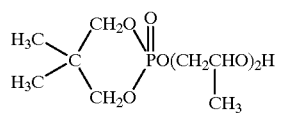 (23)

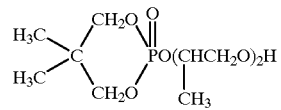 (24)

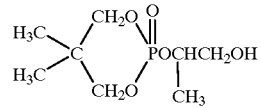 (25)

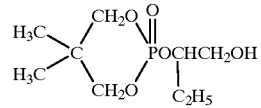 (26)

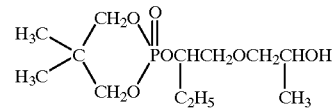 (27)

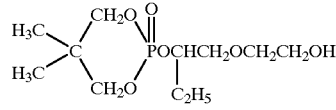 (28)

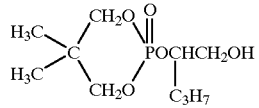 (29)

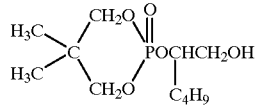 (30)

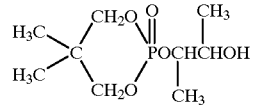 (31)

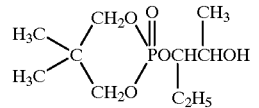 (32)

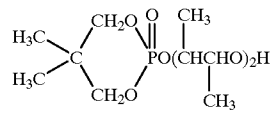 (33)

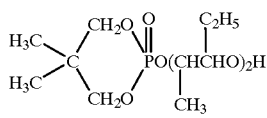 (34)

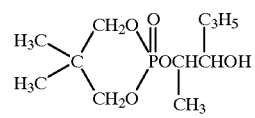 (35)

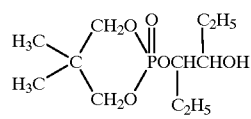 (36)

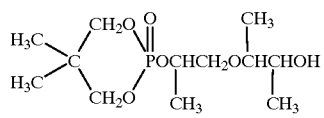 (37)

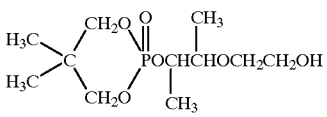 (38)

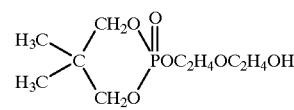 (39)

Among the compounds of the general formula (I), the compounds of the general formula (I') are novel, including the above-listed compounds (1) to (38) for example. In the general formula (I'). the substituents $R^5$, $R^6$, $R^7$, $R^8$ and y have the same meaning as defined for the substituents $R^1$, $R^2$, $R^3$, $R^4$ and x of the general formula (I), respectively. However, if both $R^5$ and $R^6$ are methyl and both $R^7$ and $R^8$ are a hydrogen atom, y is not 2.

The phosphates of the present invention may be prepared by reacting the compound of the general formula (II) with the compound of the general formula (III).

In the general formula (II), the substituents $R^1$ and $R^2$ have the same meaning as defined in the general formula (I), and preferably are methyl, ethyl, n-propyl, n-butyl, iso-propyl, iso-butyl, sec-butyl or tert-butyl, and more preferably methyl or ethyl.

The compounds (II) are novel compounds. They may be obtained by reacting a phosphorus oxyhalide with a diol compound equimolarly in an organic solvent and adding water to the resulting reaction mixture in a proportion of 2 moles of water with respect to 1 mole of the phosphorus oxyhalide for hydrolysis at about 50 to 100° C. for 0.5 to 6 hours.

The phosphorus oxyhalides used here include phosphorus oxychloride, phosphorus oxybromide, etc., among which phosphorus oxychloride is preferable from the viewpoint of workability and availability.

Examples of the diol compounds include 2,2-diethyl-1,3-propanediol, 2,2-dibutyl-1,3-propanediol, 2-ethyl-2-butyl-1,3-propanediol, neopentyl glycol, 2,2-di-n-pentyl-1,3- propanediol, 2,2-di-n-octyl-1,3-propanediol, 2,2-diphenyl-1,3-propanediol, 2,2-di(2,6-dimethylphenyl)-1,3-propanediol, 2,2-dicyclohexyl-1,3-propanediol, 2,2-diallyl-1,3-propanediol and 2,2-dibenzyl-1,3-propanediol, among which 2-ethyl-2-butyl-1,3-propanediol and neopentyl glycol are particularly preferable from the viewpoint of price and availability.

In the other material compounds (III) the substituents $R^3$ and $R^4$ have the same meaning as defined for the general formula (I), and preferably are a hydrogen atom, methyl, ethyl, n-propyl, n-butyl, iso-propyl, iso-butyl, sec-butyl or tert-butyl, and more preferably a hydrogen atom, methyl or ethyl.

Preferable examples of the compounds (III) include ethylene oxide, propylene oxide and butylene oxide.

In the reaction of the compound (II) with the compound (III), 1 to 9.5 moles, preferably 1.1 to 2 moles, of the compound (III) is used with respect to 1 mole of the compound (II). If the compound (III) is used in a molar amount less than one mole, there is left unreacted compound (II), which adversely affects the performance of the resin. If the compound (III) is used in a molar amount exceeding 9.5 moles, there are produced a large quantity of phosphates of the general formula (I) having x exceeding 9, and consequently, the phosphorus content in the obtained phosphate product declines.

According to the present invention, a phosphate having a desired phosphorus content and molecular weight may be obtained by selecting the kinds and the molar ratio of the compounds (II) and (III) as needed. The reaction of the compound (II) with the compound (III) usually is a quantitative reaction. For example, if a compound of the general formula (I) having x equal to one is desired to be obtained, the compounds (II) and (III) are reacted in a proportion of 1:1.

The reaction temperature is 25 to 120° C., preferably 40 to 100° C., more preferably 60 to 90° C. The reaction time may be varied depending upon other reaction conditions, e.g., the reaction temperature, but is usually 2 to 10 hours, preferably 4 to 7 hours.

This reaction may be carried out in an organic solvent. The organic solvent is preferably inert one to the reaction. Examples of such organic solvents include hydrocarbon solvents such as hexane, cyclohexane, heptane, octane, benzene, toluene, xylene and petroleum spirits, halogen-containing hydrocarbon solvents such as chloroform, carbon tetrachloride, chloroethane and chlorobenzene, ether solvents such as diethyl ether, diisopropyl ether, dibutyl ether, dioxane and trioxane, and nitrogen-containing hydrocarbon solvents such as acetonitrile, benzonitrile, among which toluene is particularly preferable.

A liquid phosphate product may be obtained by removing the organic solvent from the reaction mixture thus obtained.

In some cases, the obtained phosphate product contains, as impurities, unreacted materials and/or by-products such as diphosphate compounds. In such cases, the phosphate product may be refined by a known method such as distillation, washing or chromatography. However, the phosphate product containing a small amount of impurities, if used as a flame-retarder, hardly has adverse effect practically on the thermal resistance and flame retardancy of the resin composition. Refinement may be unnecessary in usual cases.

If the phosphate of the present invention is produced by the process for preparing the compound (IV) disclosed by Japanese Unexamined Patent Publication No. SHO 55(1980)-110175, i.e., by mixing an alcohol and an amine in toluene and adding phosphorus oxychloride to the resulting mixture, the obtained phosphorus product is solid because compounds like diphosphite compounds and diphosphate compounds are produced as by-products. According to the phosphate-preparing process of the present invention, on the other hand, the generation of by-products is inhibited, and therefore, the phosphate product is obtained in liquid.

The flame-retarder of the present invention is featured by containing one or a mixture of two or more of compounds obtained by reacting the compound (II) with one or more of the compounds (III), especially one or a plurality of phosphates of the general formula (I). The flame-retarder may be added in use to a material to which flame retardancy is to be given.

Examples of materials to be given flame retardancy include a variety of resins, rubbers such as natural rubbers, which are used for coating wires, styrene-butadiene rubber, polyisopropylene rubber, nitrile rubber and chloroprene rubber, fibers such as natural fibers, protein fibers and synthetic fibers, wood, paints, adhesives, coating materials, and various kinds of inks. Especially, the flame-retarder is suitably used for resins. Detailed discussion about the flame-retarder of the present invention being used for resins will be made below in a part related to flame-retarded resin compositions.

The flame-retarder of the present invention may contain another flame-retarder and/or various additives as required in such amount that they do not impair the properties of the materials to which flame retardancy is to be given.

Examples of other flame-retarders are flame-retarders of non-halogen compounds, halogen compounds or inorganic compounds, and examples of the additives are antioxidants and fillers. Further, the flame-retarder of the present invention may also contain additives such as a lubricant, stabilizer, coloring agent, antistatic agent, nucleating agent and blooming inhibitor.

The flame-retarded resin composition of the present invention contains a thermoplastic or thermosetting resin and a phosphate of the general formula (I).

Examples of the thermoplastic resins include resins such as polyethylene, chlorinated polyethylene, polypropylene, polybutadiene, polymethylpentene, poly-1-butene, polystyrene, impact-resistant polystyrene, polymethacrylstyrene, polymethyl methacrylate, polyphenylene ether, polyphenylene sulfide, polyphenylene oxide, modified polyphenylene oxide, polyacrylonitrile, polyamide (nylon), polyethylene terephthalate, polybutylene terephthalate, polycarbonate, polyvinyl alcohol, polyvinyl acetal, polyacetal, polyacrylate, polysulfone, polyester, hydroxybenzoic acid type polyester, polyvinyl chloride, polyvinyl bromide, polyvinyl fluoride, polyvinyl acetate, polyvinylidene chloride, acrylonitrile-styrene(AS) resin, acrylonitrile-butadiene-styrene(ABS) resin and acrylonitrile-chlorinated polyethylene-styrene(ACS) resin, fluorin plastics, methacrylate resin, acrylic resin, polycarbonate-ABS resin (alloy resin), vinyl chloride-styrene copolymer, vinyl chloride-ethylene copolymer, vinyl chloride-propylene copolymer, vinyl chloride-isobutylene copolymer, vinyl chloride-vinylidene chloride copolymer, vinyl chloride-chlorinated propylene copolymer, vinyl chloride-butadiene copolymer, vinyl chloride-isoprene copolymer, styrene-butadiene copolymer, acrylonitrile-butadiene copolymer, ethylene-vinyl acetate copolymer, ethylene-propylene copolymer, vinyl chloride-vinyl acetate copolymer, vinyl chloride-ethylene-vinyl acetate terpolymer, vinyl chloride-styrene-maleic anhydride terpolymer, vinyl chloride-styrene-acrylonitrile terpolymer, vinyl chloride-vinylidene chloride-vinyl acetate terpolymer, vinyl chloride-acrylic ester copolymer, vinyl chloride-maleic acid ester copolymer, vinyl chloride-methacrylic acid ester copolymer, vinyl chloride-acrylonitrile copolymer, acrylic acid ester-butadiene-styrene terpolymer, and methacrylic acid ester-butadiene-styrene terpolymer.

Among the above-listed examples, resins such as polyethylene, chlorinated polyethylene, polypropylene, polybutadiene, polystyrene, impact-resistant polystyrene, polymethyl methacrylate, polyphenylene oxide, modified polyphenylene oxide, polyamide, polycarbonate, polyester and polyvinyl chloride, AS resin, ABS resin and ACS resin are particularly preferable.

Examples of the thermosetting resins include resins such as polyurethane, phenolic resin, melamine resin, diallyl phthalate resin, polyimide, unsaturated polyester, urea resin, epoxy resin and silicone resin.

Among the above-listed examples, polyurethane, phenolic resin, melamine resin, urea resin, epoxy resin and unsaturated polyester are particularly preferable.

Preferably, the thermoplastic and thermosetting resins used in the present invention do not contain any halogen. In other words, a combination of a resin not containing halogen and the flame-retarder of a non-halogen compound is preferable because it completely avoids the risk of generation of a harmful, toxic halogen-containing gas.

Further, these resins may be used as a mixture of two or more thereof. For example, polyurethane may preferably be combined with a melamine resin or a urea resin in view of obtaining a well-balanced flame retardancy, mechanical properties and bleeding characteristic.

Among the above-listed thermoplastic and thermosetting resins, impact-resistance polystyrene, ABS resin and polyurethane are more preferable, and polyurethane is particularly preferable.

In the case where polyurethane is used as the resin of the flame-retarded resin composition of the present invention, at the synthesis of polyurethane, i.e., at polyaddition reaction of a polyol and diisocyanate which are materials for polyurethane, hydroxyl groups in the phosphate of the present invention react with diisocyanate and the phosphate is incorporated in the polyurethane. The resulting polyurethane has a smooth surface without exudation of the additives such as the phosphate onto the surface, is excellent in fogging properties, resistance to hydrolysis and scorch characteristic, and may retain a long-lasting flame retardancy.

The flame-retarded resin composition of the present invention may contain an antioxidant and other kinds of additives as required in such amount that does not impair the properties of the composition. The additives can give higher added-values to the resin composition. Among the additives, the antioxidant is particularly effective.

Examples of the additives include flame-retarders of non-halogen compounds, halogen compounds or inorganic compounds, antioxidants and fillers. Further the flame-retarded resin composition of the present invention may also contain additives such as a lubricant, stabilizer, coloring agent, antistatic agent, nucleating agent and blooming inhibitor.

Examples of the non-halogen compounds include phosphates such as triphenyl phophate, trixylyl phosphate, trimethyl phosphate, tributyl phosphate and their condensates (e.g., CR-733S, CR-741, CR-747 and PX-200 produced by Daihachi Chemical Industries Co., Ltd.).

Examples of the halogen compounds include halogen-containing phosphates such as tris(β-chloroethyl)phosphate and tris(2,3-dibromopropyl)phosphate, halogen compounds such as tetrabromoethane and hexabromocyclodecane, dechloran plus (trade name of an organic halogen flame-retarder produced by Occidental Chemical Co.), and hexabromocyclododecane.

Examples of the inorganic compounds include magnesium hydroxide, aluminum hydroxide and antimony oxide. These inorganic compounds are preferably used in combination with the organic phosphorus compound of the present invention especially when the resin is a modified polyphenylene oxide, polystyrene or ABS resin.

Examples of the antioxidants include trivalent phosphorus compounds, hydroquinone compounds, phenol compounds, amine compounds and sulfur compounds, among which hydroquinone compounds and trivalent phosphorus compounds are preferable. These antioxidants may be used individually or as a mixture of two or more thereof. The antioxidants may provide a good thermal resistance and fogging properties for the resin composition.

Preferable examples of the hydroquinone compounds include hydroquinone, 2,5-di-tert-butylhydroquinone, 2,5-tert-amylhydroquinone and octylhydroquinone, among which 2,5-tert-amylhydroquinone is particularly preferable in that it improves the thermal resistance of the flame-retarded resin composition.

Preferable examples of the trivalent phosphorus compounds include triphenyl phosphite, tris(nonylphenyl) phosphite, diphenylisodecyl phosphite, bis(2,4-di-tert-butylphenyl)pentaerythritol diphosphite and tetrakis(2,4-di-tert-butylphenyl)-4,4-diphenylene phosphonite.

The use amount of the antioxidant may be varied depending upon the kind and amount of the resin and other ingredients, but is preferably 0.5 to 5 wt % to the phosphate. If the antioxidant is used in an amount within the above-mentioned range, a good antioxidant effect can be obtained.

Examples of the fillers include silica, talc, graphite, carbon black, titanium oxide and alumina.

Examples of the lubricants include liquid paraffin, natural paraffin, fluorocarbon, higher fatty acids, fatty amides, esters and fatty alcohols.

The kind and amount of the phosphates in the flame-retarded resin composition of the present invention may be selected as needed depending upon the resin to be used, intended use, required properties and required degree of flame retardancy of an article to be made from the composition.

The phosphates, as flame-retarders, are used in a proportion of 0.1 parts by weight or more, preferably 0.1 to 50 parts by weight, more preferably 3 to 50 parts by weight, still more preferably 5 to 15 parts by weight, with respect to 100 parts by weight of the resin. If the amount of the phosphate is less than 0.1 parts by weight, satisfactory flame retardancy may not be obtained.

The flame-retarded resin composition of the present invention is obtained by mixing and kneading the above-described resin, the compound obtained by the reaction of the compound (II) with one or more of the compound (III) especially the phosphate of the general formula (I), and one or more of the above-mentioned additives by a known method. For kneading, usable is an apparatus such as a single-screw extruder, twin-screw extruder, Banbury mixer or kneader mixer.

The order of adding the components and the way of mixing them are not particularly limited, but for example, the flame retardancy may be given to the resin composition by ① adding the phosphate of the present invention to monomers fed when the resin is produced by bulk polymerization, ② adding the phosphate at the last stage of the reaction of the bulk polymerization of the resin, or ③ adding when the resin is formed.

The resin composition may be formed into a variety of desired shapes by known methods, that is, the composition may be formed into flame-retarded articles in the form of plate, sheet, film or the like.

EXAMPLES

The present invention is now explained in detail by way of the following examples, which should not be construed to limit the scope of the invention. In the examples, the term "part(s)" means "part(s) by weight" unless otherwise indicated.

analysis of Compound 1 together with its theoretical values, and FIG. 1 shows the result of gel permeation chromatography (GPC) thereof.

In FIG. 1, measured intensity is plotted in ordinate, and peaks n1, n2 and n3 correspond to compounds of the general formula (I) wherein x is 1, 2 and 3, respectively. FIG. 1 shows that Compound 1 contains 64.9%, 19.2% and 5.5% of the compounds corresponding to the peaks n1, n2 and n3, respectively.

Figure 2:
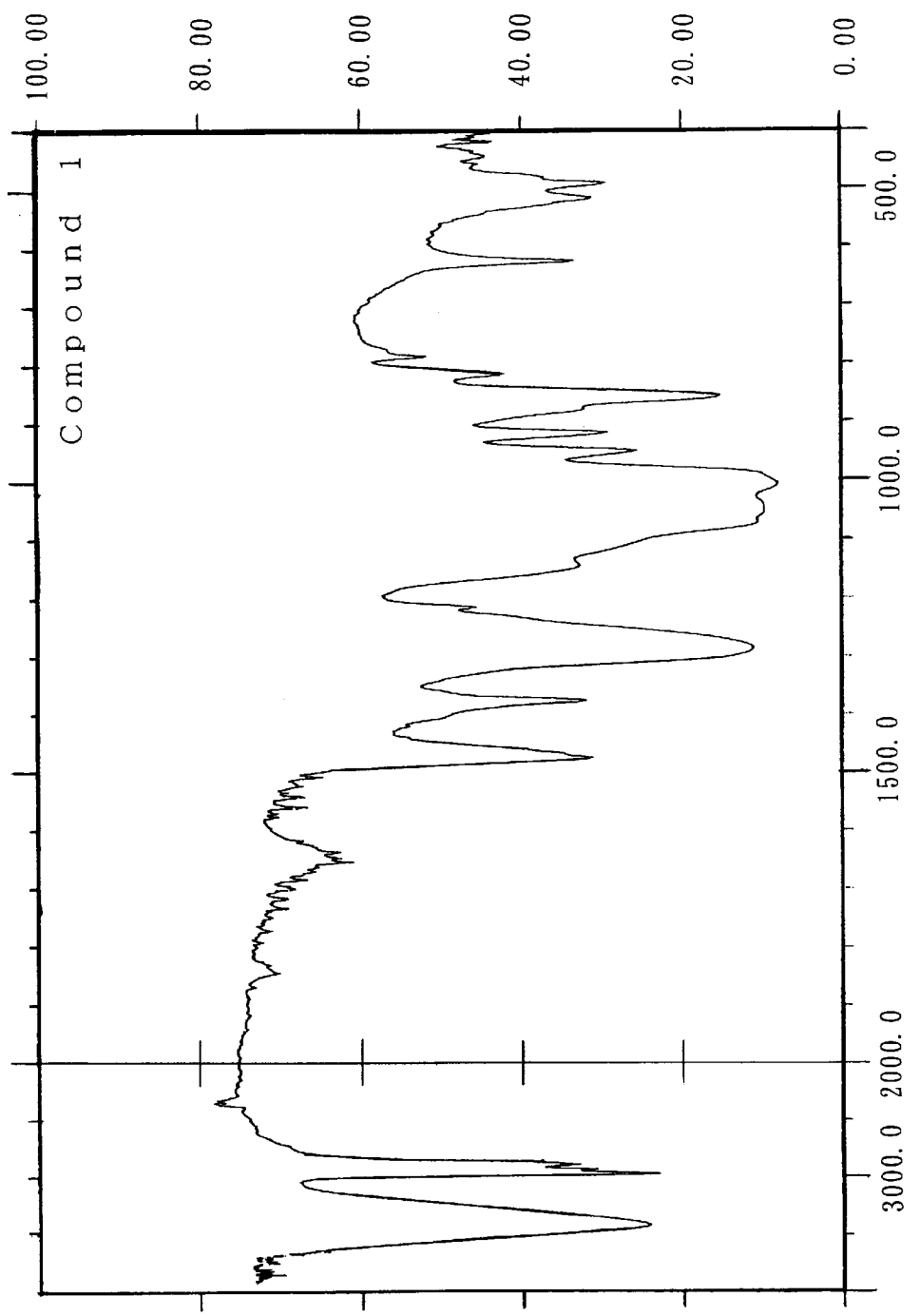
FIG. 2 shows a result of IR of the phosphate (Compound 1) of the present invention.
Figure 3:
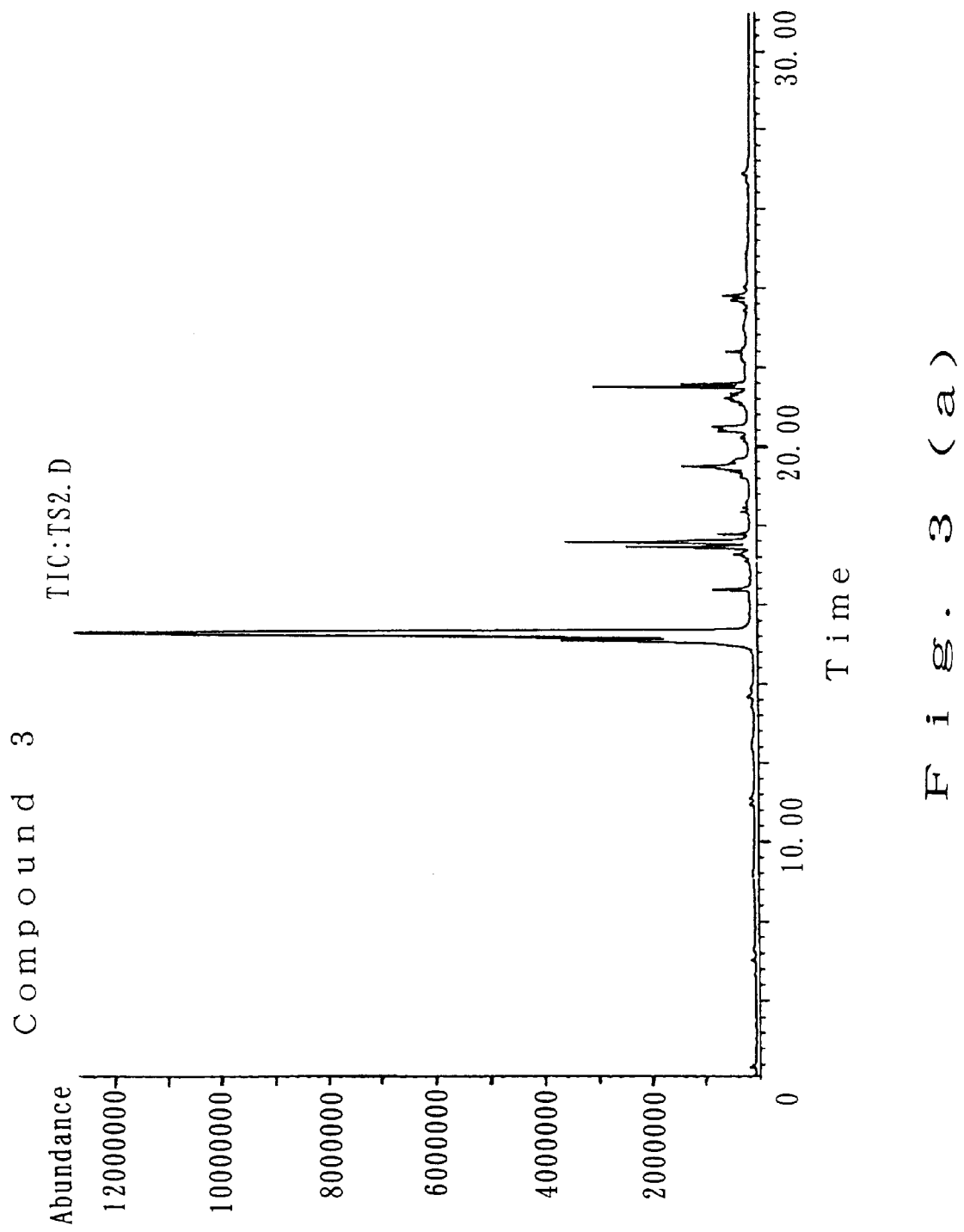
FIGS. 3(a) and 3(b) show a result of GC-MS of the phosphate (Compound 1) of the present invention.
Figure 3:
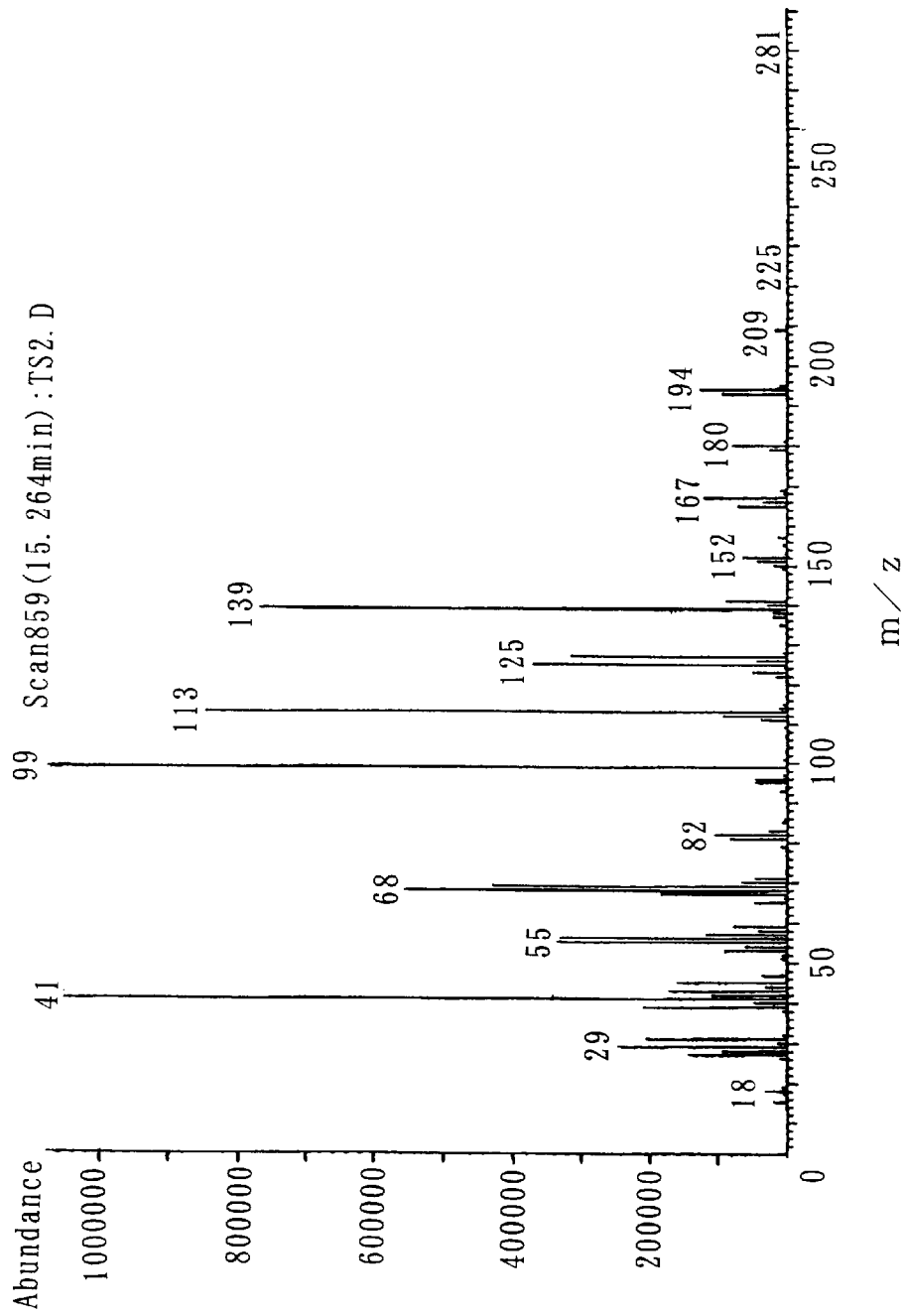

FIGS. 2, 3(a) and 3(b) show the results of infrared absorption spectroscopy (IR) and gas chromatography-mass spectrometry (GC-MS) of Compound 1.

In a GC chart of FIG. 3(a), the peak of 15.264 min. corresponds to the compound showing the peak n1 in the above GPC. In an MS chart of FIG. 3(b), the peak of 225 ($m^+$+1) corresponds to the compound showing the peak n1 in the above GPC, and the peak of 165 ($M^+$) corresponds to a compound of the following formula:

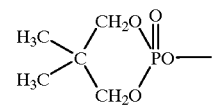

TABLE 1

|  | Yield (%) | Viscosity (cps) | Elemental Analysis | | | | | | | |
|---|---|---|---|---|---|---|---|---|---|---|
|  |  |  | Theoretical Values (%) | | | | Measured Values (%) | | | |
|  |  |  | C | H | O | P | C | H | O | P |
| Example 1 | 98 | 4000 | 44.1 | 7.7 | 35.1 | 13.1 | 44.8 | 7.6 | 34.7 | 12.9 |
| Example 2 | 96 | 1050 | 40.6 | 7.2 | 38.0 | 14.2 | 40.9 | 7.4 | 37.9 | 13.8 |
| Example 3 | 98 | 860 | 47.3 | 7.9 | 36.1 | 8.7 | 47.4 | 7.9 | 36.1 | 8.6 |

Example 1

Into a one-liter four-necked flask provided with a stirrer, a thermometer and a condenser connected to a water scrubber, 104 g (1 mole) of neopentyl glycol and 100 g of toluene were f ed and heated with stirring. Then, while the mixture was maintained at 50° C. with a thermostat, 153.5 g (1 mole) of phosphorus oxychloride were added to the mixture in an hour. After the addition of phosphorus oxychloride, the resulting mixture was stirred at the same temperature for four hours for completion of dehydrochlorination. Then, 36 g (2 moles) of water were added to the resulting mixture, which was then stirred at 80° C. for about 4 hours. Then, excess water was collected. While maintaining the reaction mixture at 80° C., 72 g (1.24 moles) of propylene oxide were added to the mixture in 2 hours. After the addition of propylene oxide, the resulting mixture was stirred at the same temperature for 4 hours. Then, toluene was collected under reduced pressure, and thus the object product was obtained.

The obtained product (hereinafter referred to as Compound 1) was transparent liquid, and the yield thereof was 235 g (in a 98% yield). Table 1 shows the result of elemental Compound 1 is considered to be a mixture of compounds having the following formula. The "1.2" in the formula represents a mean value of x.

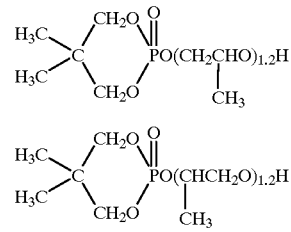

Example 2

An object compound was obtained by following the process of Example 1 except that 53 g (1.24 moles) of ethylene oxide were used in place of 72 g of propylene oxide. The obtained product was identified by GPC and IR.

Figure 4:
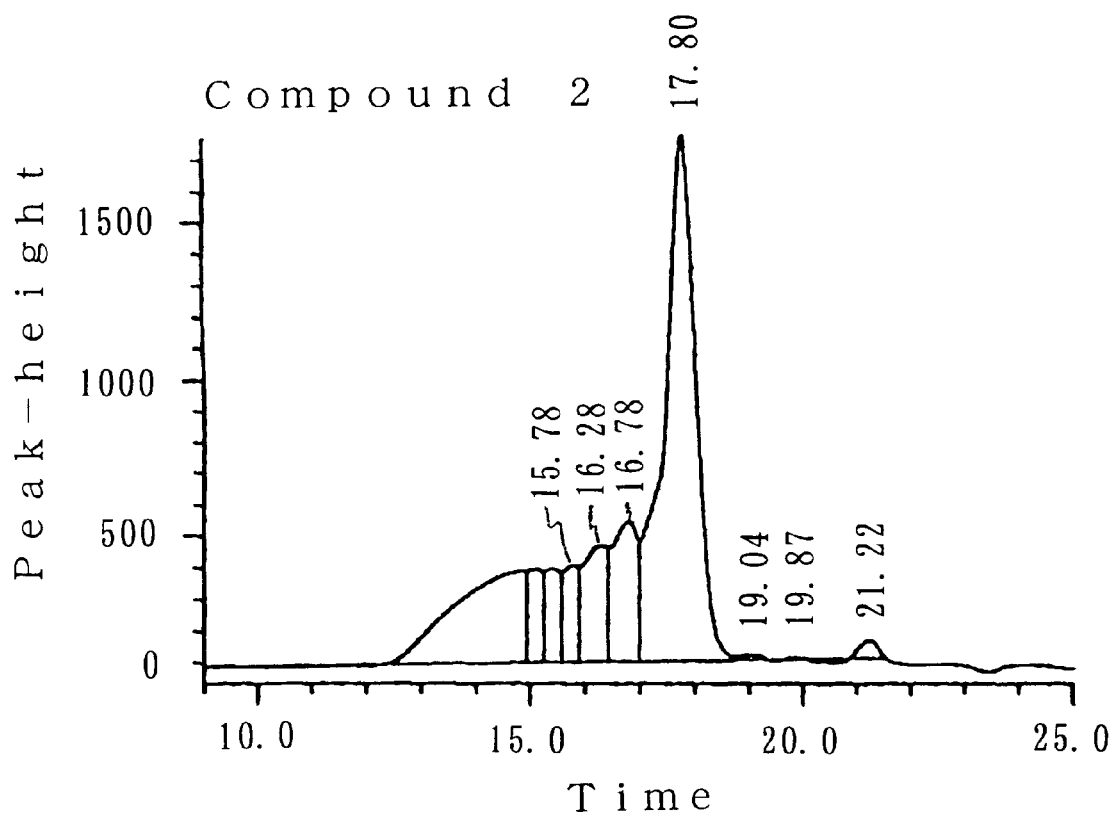
FIGS. 4 shows a result of GPC of a phosphate (Compound 2) in accordance with Example 2 of the present invention.
Figure 5:
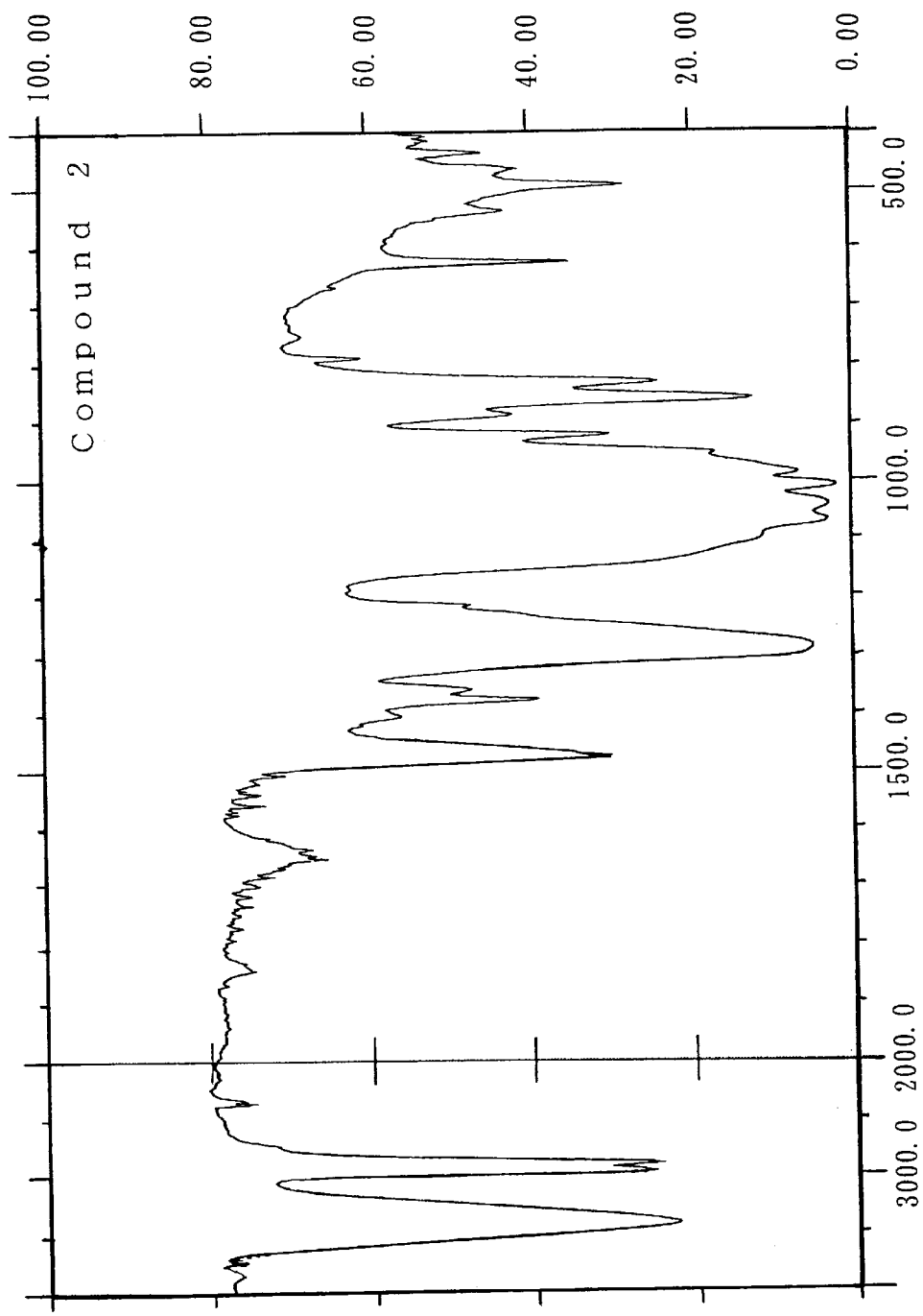
FIG. 5 shows a result of IR of the phosphate (Compound 2) of the present invention.

The obtained product (hereinafter referred to as Compound 2) was transparent liquid, and the yield thereof was 210 g (in a 96% yield). Table 1 also shows the result of the elemental analysis conducted on Compound 2 in the same manner as in Example 1 together with its theoretical values. FIGS. 4 and 5 show the results of GPC and IR, respectively.

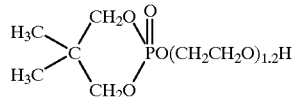

Example 3

An object product was obtained by following the process of Example 1 except that 160 g (1 mole) of ethylbutylpropanediol were used in place of 104 g of neopentyl glycol. The obtained product was identified by GPC and IR.

Figure 6:
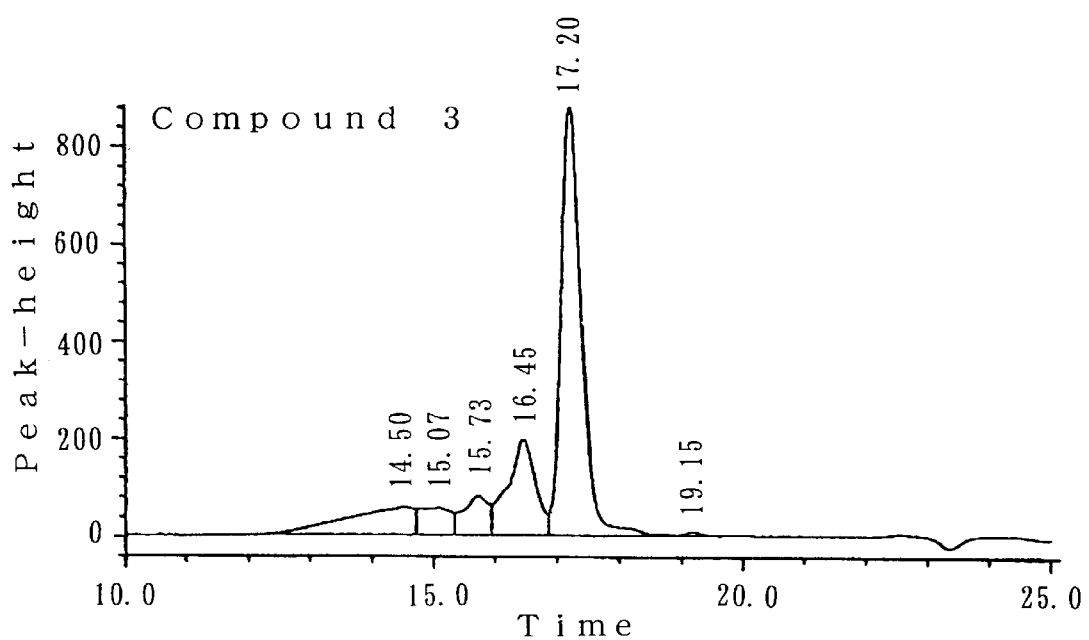
FIG. 6 shows a result of GPC of a phosphate (Compound 3) in accordance with Example 3 of the present invention.
Figure 7:
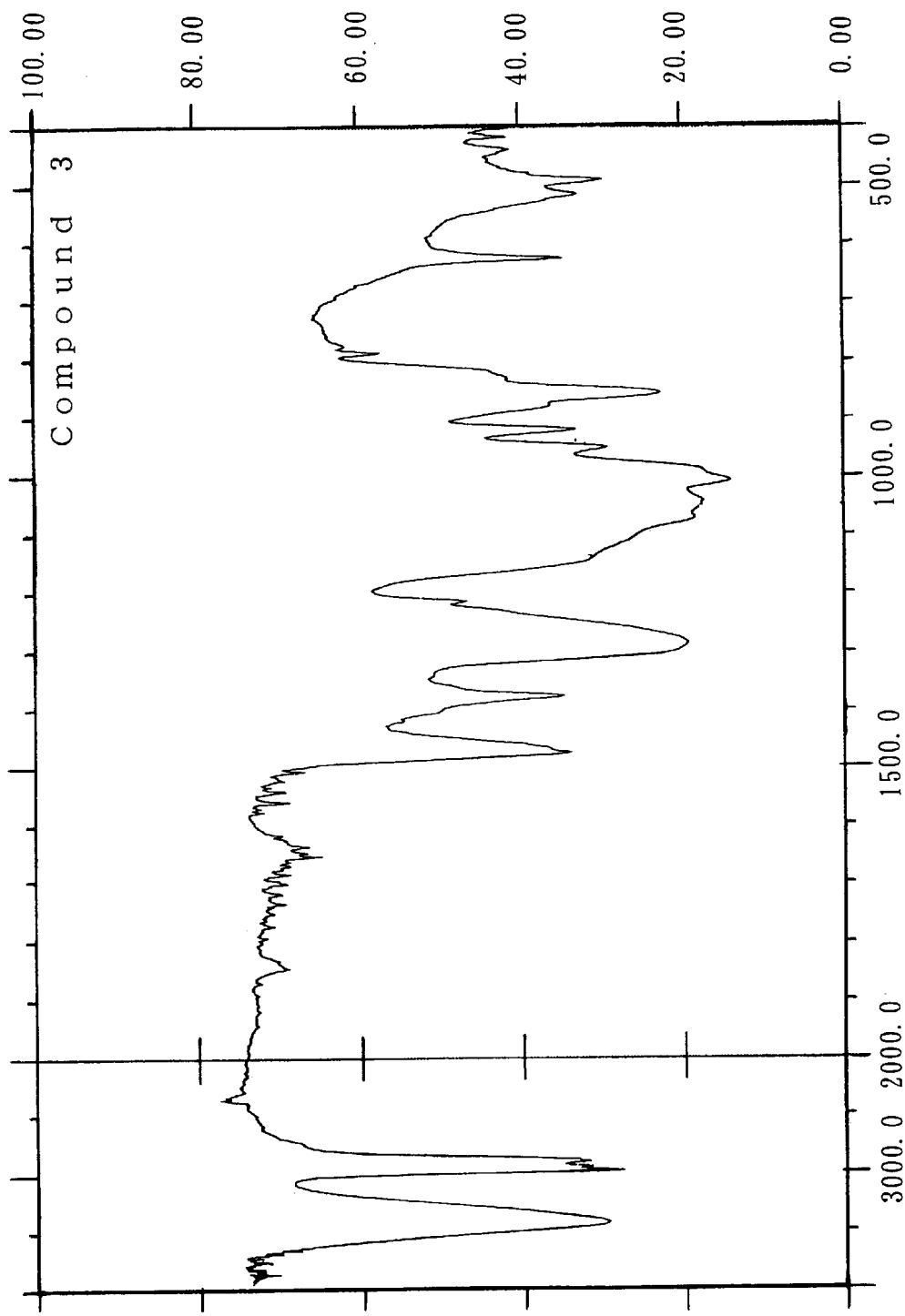
FIG. 7 shows a result of IR of the phosphate (Compound 3) of the present invention.

The obtained product (hereinafter referred to as Compound 3) was transparent liquid, and the yield thereof was 270 g (in a 98% yield). Table 1 also shows the result of the elemental analysis conducted on Compound 3 in the same manner as in Example 1 together with its theoretical values. FIGS. 6 and 7 show the results of GPC and IR, respectively.

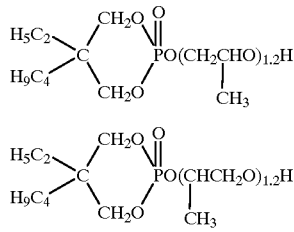

Some of the phosphate products obtained in the above-described examples contained by-products, but they were used without being refined in the following evaluation of performance, because the by-products were considered not to affect the thermal resistance or flame retardancy of resin compositions in which the phosphate products were used as flame-retarders.

In the following examples, in addition to the above Compounds 1 to 3, conventional flame-retarder compounds A to F as shown below were also evaluated on their performance for comparison:

Compound A

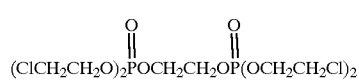

Compound B

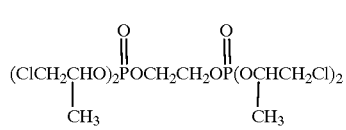

Compound C

Compound D

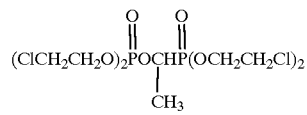

Compound E

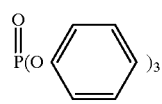

Compound F

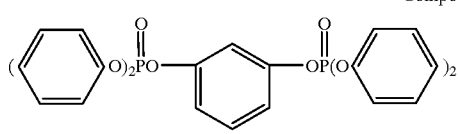

Example 4

Components of Flame-retarded resin Compositions

| | |
|---|---|
| Polyol (trade name: MN-3050 ONE produced by Mitsui Toatsu Chemicals Inc., Japan) | 100 parts |
| Diisocyanate (trade name: TDI 80/20 produced by Mitsui Toatsu Chemicals Inc.) | 55.1 parts |
| Polyol silicone oil (trade name: L-520 produced by Nippon Unicar Co., Ltd., Japan) | 1.2 parts |
| Tin-base catalyst (dibutyltin dilaurate) | 0.25 parts |
| Amine-base catalyst (trade name: Kaolizer No. 1 produced by Kao Corp., Japan) | 0.15 parts |
| Water | 4.5 parts |
| Methylene chloride | 3.0 parts |
| Flame retarder (in an amount shown in Table 2) | |

The above-mentioned components were used to produce flexible urethane foam by a one-shot process as described below. At that time, hydroquinone (HQ) and triphenyl phosphite (TP-I) as antioxidants were added to the flame-retarder.

First, of the above-mentioned components, polyol, silicone oil, catalyst, methylene chloride, water and the flame-retarder were mixed and stirred with a stirrer at 3,000 rpm for a minute to obtain a uniform mixture. Then, diisocyanate was added to the mixture, which was further mixed at 3,000 rpm for 5 to 7 seconds and then, rapidly poured into a board-carton box of square cross section. Expansion took place immediately and the foam reached its maximum volume in several minutes. Then the foam was allowed to cure in an oven at 120° C. for 30 minutes. The obtained foam was white, flexible and had open cells.

Samples were taken from foams obtained in the above-described manner and subjected to a combustion test of MVSS-302. Samples were taken again, microwaved for 3 minutes using a 500 W microwave oven and then heated at 140° C. for 2 hours. Changes in color of the samples (the presence or absence of scorch) were observed.

Results are shown in Table 2. In the column of "scorch" in Table 2, the sign ○ indicates that change in the color was hardly observed, and the sign × indicates that the samples turned brown. The sign "SE" in the item of average combustion distance indicates "self-extinguishing" and the sign "NB" indicates "non-burning." The item (YI) represents degree of yellow in the center of the foams measured by a chromoscope.

TABLE 2

| Flame-Retarder | (parts by weight) | HQ | TP-I | Mean Combustion Distance (mm) | (parts by weight) | Mean Combustion Distance (mm) | (parts by weight) | (YI) | Scorch |
|---|---|---|---|---|---|---|---|---|---|
| Compound 1 | 8 | | | NB 32.0 | 10 | NB 21.3 | 20 | 40 | ○ |
|  | 8 | 0.08 | 0.08 | NB 32.3 | 10 | NB 21.3 | 20 | 25 | ○ |
| Compound 2 | 8 | | | NB 28.6 | 10 | NB 19.2 | 20 | 50 | ○ |
|  | 8 | 0.08 | 0.08 | NB 28.4 | 10 | NB 19.5 | 20 | 30 | ○ |
| Compound A | 8 | | | SE 39.6 | 10 | NB 27.8 | 20 | 90 | × |
| Compound B | 8 | | | — | 10 | SE 75.0 | 20 | 70 | Δ |
| Compound C | 8 | | | SE 76.0 | 10 | SE 52.0 | 20 | 40 | ○ |
| Compound D | 8 | | | NB 31.0 | 10 | NB 21.6 | 20 | 95 | × |
| not used | — | | | Burnt out | | | | 30 | ○ |

As clearly seen from Table 2, the resin compositions containing the phosphates of the present invention exhibit a better flame retardancy and are free of scorching, compared with the resin compositions containing the conventional halogen-containing flame-retarders.

The flame-retarded resin compositions of the present invention were allowed to stand at 80° C. for 14 days. There were not observed any changes in their flame retardancy.

Example 5

Compounds shown in Table 3 (10 parts) were each added to 100 parts of a mixture of impact-resistant polystyrene/PPO resin (45/55). The resulting mixtures were uniformly mixed for about 15 minutes in a 10-liter V-type blender. The mixtures were made into pellets by an extruder having a 40 mm inner diameter. The pellets were made into test samples by a molding machine having a 4 oz. volume.

The test samples were evaluated on their flame retardancy in accordance with the test method defined in UL-94. More particularly, time from the catching of fire to the extinction of fire was counted and averaged for five test samples of each resin composition. As for juicing, surfaces of articles made of the resin compositions were observed by eye inspection. Thermal deformation temperature was measured in accordance with the test method defined in ASTM D648.

The results are shown in Table 3.

TABLE 3

|  | Time to Extinction of Fire (seconds) | Thermal Deformation Temperature (° C.) | Juicing |
|---|---|---|---|
| Compound 2 | 32 | 96.3 | No |
| Compound 3 | 39 | 95.1 | No |

TABLE 3-continued

|  | Time to Extinction of Fire (seconds) | Thermal Deformation Temperature (° C.) | Juicing |
|---|---|---|---|
| Compound E | Fire did not go out | 81.5 | Yes |
| Compound F | 45 | 86.0 | A little |

Example 6

Ten parts (10 parts) of compounds shown in Table 4, 5 parts of tetrabromobisphenol A and 2.5 parts of antimony trioxide were added to 100 of ABS resin (Cevian-V produced by Daicel Chemical Industries Co., Japan). The resulting mixtures were uniformly blended for about 15 minutes in a 10-liter V-type blender. The mixtures were made into pellets by an extruder having a 40 mm inner diameter. The pellets were made into test samples by a molding machine having a 4 oz. volume.

The obtained test samples were evaluated on their flame retardancy and juicing in the same manner as in Example 5. Results are shown in Table 4.

TABLE 4

|  | Time to Extinction of Fire (seconds) | Thermal Deformation Temperature (° C.) | Juicing |
|---|---|---|---|
| Compound 1 | 9 | 89.3 | No |
| Compound 2 | 6 | 94.3 | No |
| Compound E | 20 | 75.3 | Yes |
| Compound F | 14 | 80.2 | A little |

The phosphates of the present invention may provide various kinds of resins with an excellent flame-retardancy.

The phosphates are liquid at room temperature and little volatile, and has a good miscibility to resins. When reacted with a resin component in use, the phosphates enable the resins to maintain a high flame retardancy for a long time.

Further, the phosphates of the present invention are also excellent in thermal resistance, and therefore, the phosphates do not cause the coloring and deterioration of the resins by thermolysis at molding, extrusion or the like of the resins. Furthermore, the extrusion or the like of the resins. Furthermore, the flame-retarded resin composition of the present invention has a remarkable resistance to heat and hydrolysis, and can be made into articles which do not generate drips of molten resin when the articles catch fire.

What is claimed is:

1. A flame retarder containing a phosphate obtainable by reacting a compound represented by the general formula (II):

$$\begin{array}{c} R^1 \\ \phantom{R^1} \diagdown \\ \phantom{R^1} \phantom{\diagdown} C \\ R^2 \diagup \phantom{C} \diagdown \end{array} \begin{array}{c} CH_2O \\ \phantom{CH_2O} \diagdown \\ \phantom{CH_2O} \phantom{\diagdown} POH, \\ CH_2O \diagup \end{array} \qquad (II)$$

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, with at least one compound represented by the general formula (II):

$$R^3HC \underset{O}{-\!\!\!-\!\!\!-} CHR^4, \qquad (III)$$

wherein $R^3$ and $R^4$ are, the same or different, a hydrogen atom or a straight or branched-chain alkyl group having 1 to 8 carbon atoms.

2. A flame-retarder according to claim 1, wherein the compound represented by the general formula (III) is selected from ethylene oxide, propylene oxide and butylene oxide.

3. A flame retarded resin composition comprising a thermoplastic or thermosetting resin and a phosphate as set forth in claim 1 in an effective amount as a retarder.

4. A flame retarded resin composition according to claim 3, wherein 0.1 to 50 parts by weight of the phosphate are contained with respect to 100 parts by weight of the resin.

5. A flame retarded resin composition according to claim 4, wherein 3 to 50 parts by weight of the phosphate are contained with respect to 100 parts by weight of the resin.

6. A flame retarded resin composition according to claim 3, wherein the resin does not contain halogen.

7. A flame retarded resin composition according to claim 6, wherein the resin not containing halogen is a polyurethane.

8. A flame retarded resin composition according to claim 3 further containing an antioxidant.

9. A flame retarded resin composition according to claim 8, wherein the antioxidant is a hydroquinone compound selected from the group consisting of hydroquinone, 2,5-di-tert-butylhydroquinone, 2,5-tert-amylhydroquinone and octylhydroquinone, or an organic phosphorous compound selected from the group consisting of triphenyl phosphate, tris(nonylphenyl)phosphite, diphenylisodecyl phosphite, bis (2,4-di-tert-butylphenyl)pentaerythritol diphosphite and tetrakis(2,4-di-tert-butylphenyl)-4,4-diphenylene phosphonite.

10. A process for preparing a phosphate, the process comprising reacting a compound represented by the general formula (II):

$$\begin{array}{c} R^1 \\ \phantom{R^1} \diagdown \\ \phantom{R^1} \phantom{\diagdown} C \\ R^2 \diagup \phantom{C} \diagdown \end{array} \begin{array}{c} CH_2O \\ \phantom{CH_2O} \diagdown \\ \phantom{CH_2O} \phantom{\diagdown} POH \\ CH_2O \diagup \end{array} \qquad (II)$$

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, with a compound represented by the general formula (III):

$$R^3HC \underset{O}{-\!\!\!-\!\!\!-} CHR^4 \qquad (III)$$

wherein $R^3$ and $R^4$ are, the same or different, a hydrogen atom or a straight or branched-chain alkyl group having 1 to 8 carbon atoms, to obtain a phosphate represented by the general formula (I):

$$\begin{array}{c} R^1 \\ \phantom{R^1} \diagdown \\ \phantom{R^1} \phantom{\diagdown} C \\ R^2 \diagup \phantom{C} \diagdown \end{array} \begin{array}{c} CH_2O \\ \phantom{CH_2O} \diagdown \\ \phantom{CH_2O} \phantom{\diagdown} PO(CHCHO)xH \\ CH_2O \diagup \phantom{PO(}\!R^3\ R^4 \end{array} \qquad (I)$$

wherein $R^1$, $R^2$, $R^3$ and $R^4$ are defined as above and x is an integer of 1 to 9.

11. A phosphate represented by the general formula (II):

$$\begin{array}{c} R^1 \\ \phantom{R^1} \diagdown \\ \phantom{R^1} \phantom{\diagdown} C \\ R^2 \diagup \phantom{C} \diagdown \end{array} \begin{array}{c} CH_2O \\ \phantom{CH_2O} \diagdown \\ \phantom{CH_2O} \phantom{\diagdown} POH, \\ CH_2O \diagup \end{array} \qquad (II)$$

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms.

12. A flame retarder containing a phosphate represented by the general formula (I):

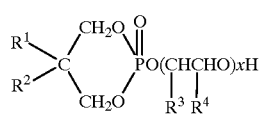

wherein $R^1$ and $R^2$ are, the same or different, a straight or branched-chain alkyl group having 1 to 8 carbon atoms, an alkenyl group having 2 to 8 carbon atoms, an optionally substituted aryl group having 6 to 12 carbon atoms, an alicyclic hydrocarbon group having 3 to 12 carbon atoms or an aralkyl group having 7 to 12 carbon atoms, wherein $R^3$ is a straight chain alkyl having 2 to 8 carbon atoms, or branched-chain alkyl group having 3 to 8 carbon atoms, $R^4$ is a hydrogen atom or a straight or branched-chain alkyl group having 1 to 8 carbon atoms, and x is an integer of 1 to 9.

13. The flame-retarder according to claim 12, wherein $R^1$ and $R^2$ are each a lower alkyl group having 1 to 4 carbon atoms and x is an integer of 1 to 5.

14. The flame-retarder according to claim 13, wherein $R^1$ and $R^2$ are each methyl or ethyl and $R^3$ is ethyl.

* * * * *